United States Patent [19]

Loda

[11] Patent Number: 5,858,179
[45] Date of Patent: Jan. 12, 1999

[54] METHOD OF TREATING KERATINIC FIBERS SUCH AS A MAMMALIAN HAIR WITH A COMBINATION OF CHEMICALS AND ELECTROMAGNETIC RADIATION

[75] Inventor: Richard T. Loda, Laguna Niguel, Calif.

[73] Assignee: Intertec Ltd., Mill Valley, Calif.

[21] Appl. No.: 937,543

[22] Filed: Sep. 25, 1997

[51] Int. Cl.$^6$ .................................................. C07C 1/00
[52] U.S. Cl. ........................................... 204/157.15
[58] Field of Search ........................................ 204/157.15

[56] References Cited

U.S. PATENT DOCUMENTS 5,395,490  3/1995  Hoff et al. ............................ 204/132

FOREIGN PATENT DOCUMENTS 1260227  1/1972  United Kingdom .

*Primary Examiner*—Kathryn Gorges
*Assistant Examiner*—Edna Wong
*Attorney, Agent, or Firm*—Elmer Galbi

[57] ABSTRACT

A combination of chemicals and electromagnetic radiation is used to alter the physical characteristics of keratinic fibers such as mammalian or human hair. A non-irritating, non-reactive disulfide in the form of a solution or gel is first contacted with the hair. Electromagnetic radiation is then applied to the hair to photochemically convert the disulfide into a dithiol. The dithiol breaks the disulfide bonds in the hair so that the hair can be permanently re-shaped.

16 Claims, 3 Drawing Sheets

Step 1.

Disulfide precursor
e.g. ox-DTT, lipoic acid

Resultant dithiol
e.g. DTT, dihydrolipoic acid

Step 2.

Step 3.

SH = thiol
S-S = disulfide
S = sulfur atom
H = hydrogen atom
K = keratin (hair protein)

◯ = other moieties, may be ring or open chain.

Step 1.

Disulfide precursor
e.g. ox-DTT, lipoic acid

Resultant dithiol
e.g. DTT, dihydrolipoic acid

Step 2.

Step 3.

SH = thiol
S-S = disulfide
S = sulfur atom
H = hydrogen atom
K = keratin (hair protein)

⌒⌒ = other moieties,
may be ring or open chain.

METHOD OF TREATING KERATINIC FIBERS SUCH AS A MAMMALIAN HAIR WITH A COMBINATION OF CHEMICALS AND ELECTROMAGNETIC RADIATION

FIELD OF THE INVENTION

The present invention relates to a technique for altering the physical characteristics of keratinic fibers. More particularly the invention is directed to treating keratinic fibers such as mammalian hair with a combination of chemicals and electromagnetic radiation.

BACKGROUND OF THE INVENTION

U.S. Pat. No. 5,395,490 describes a method of altering the physical characteristics of keratinic fibers utilizing electromagnetic radiation of a particular frequency. The technique described in U.S. Pat. No. 5,395,490 disrupts the disulfide bonds in keratinic fibers by electromagnetic radiation that has a frequency corresponding to the natural resonant frequency of the disulfide bond.

It is also well known that the disulfide bonds (S—S) in keratinic fibers can be disrupted by treating the fibers with various reactive chemicals. For example, conventional permanent waving of hair treats hair with sulfur reducing agents such as thioglycolic acid, thioglycerol, thioacetic acid or mercaptoethanol to break the disulfide bonds (For example, see book entitled "*Chemical and Physical Behavior of Human Hair*" by C. R. Robbins, 1994). Treatment with these chemicals is usually followed by treatment with a neutralizing agent such as peroxide to reestablish the disulfide bonds. All of the conventionally used chemicals for permanently waving hair have various disadvantages. For example some of the chemicals damage the hair and leave it feeling harsh. Others require mixing immediately prior to use since they hydrolyze on contact with water. Also, they are all reactive compounds and begin reacting as soon as they are applied to the hair, making even application difficult, and the desired resultant uniform hair reduction over the whole head complicated.

It has also been suggested that ring forming dithiols are effective in disrupting disulfide bonds to permanently wave hair. For example see U.K. Patent 1,260,227. However, ring forming dithiols have not previously achieved any significant commercial success as chemicals for permanently waving.

Attempts have been previously made to effect the hair reduction and neutralization reactions in a single operation (For example, see book entitled "*The Science of Hair Care*", C. Zviak (ed.), Vol. 7, Dermatology Series, pg. 194–195, 1986). Such a self-neutralizing system would simplify the process, achieve a permanent wave in a single step, and save considerable time. Unfortunately, none of the techniques previously investigated has led to a satisfactory self-neutralizing system that doesn't require the peroxide neutralization step, or its equivalent.

SUMMARY OF THE PRESENT INVENTION

The present invention is an improvement on the technique disclosed in U.S. Pat. No. 5,395,490. The present invention utilizes a combination of chemicals and electromagnetic radiation to alter the physical characteristics of keratinic fibers such as mammalian or human hair.

With the present invention a non-irritating, non-reactive disulfide in the form of a solution or gel is first contacted with the hair. Electromagnetic radiation is then applied to the hair to photochemically convert the disulfide into a dithiol. The dithiol breaks the disulfide bonds in the hair so that the hair can be permanently re-shaped.

In the preferred embodiment the hair is first contacted with a formulation containing an non-reactive, non-irritating disulfide optical photosensitizer, such as, lipoic acid or oxidized dithiothreitol (ox-DTT). Excess chemicals can then be rinsed off the hair and skin while the formulation is still in the non-reactive state. Next, electromagnetic radiation is directed at the hair to photolyze the disulfides into dithiols. The dithiols react upon the hair to break the disulfide bonds thereby allowing the hair to be shaped using a curler or straightening device. The photoreaction can occur both in the formulation and within the hair shaft itself. The relative amount of each depends upon the formulation details, diffusion rates, specific photosensitizer absorption, wavelength and intensity of the electromagnetic energy source, and the condition, type, and color of the hair being treated. A significant advantage of the present invention is that the reaction may be started and stopped immediately, when desired, by simply turning the light source on or off. In a conventional chemical permanent waving process, the reactive compounds begin to react immediately as they are applied to the hair and need to be fully rinsed out of the hair before the reaction can be stopped.

As a final step in the process the hair is rinsed using an oxidizing solution such as peroxide which reforms the disulfide bonds in the hair in their new configurations. The peroxide also deactivates any residual optical photosensitizer and prevents further inadvertent alteration of the shape of the hair. It has been found that for certain of the photosensitizers of this invention, especially the ring forming disulfides such as lipoic acid and oxidized dithiothreitol and their simple derivatives, the process is self-neutralizing. This means that the peroxide step is not required to achieve a permanent shaping of the hair under treatment using these materials.

DETAILED DESCRIPTION OF A PREFERRED EMBODIMENT

Figure 1:
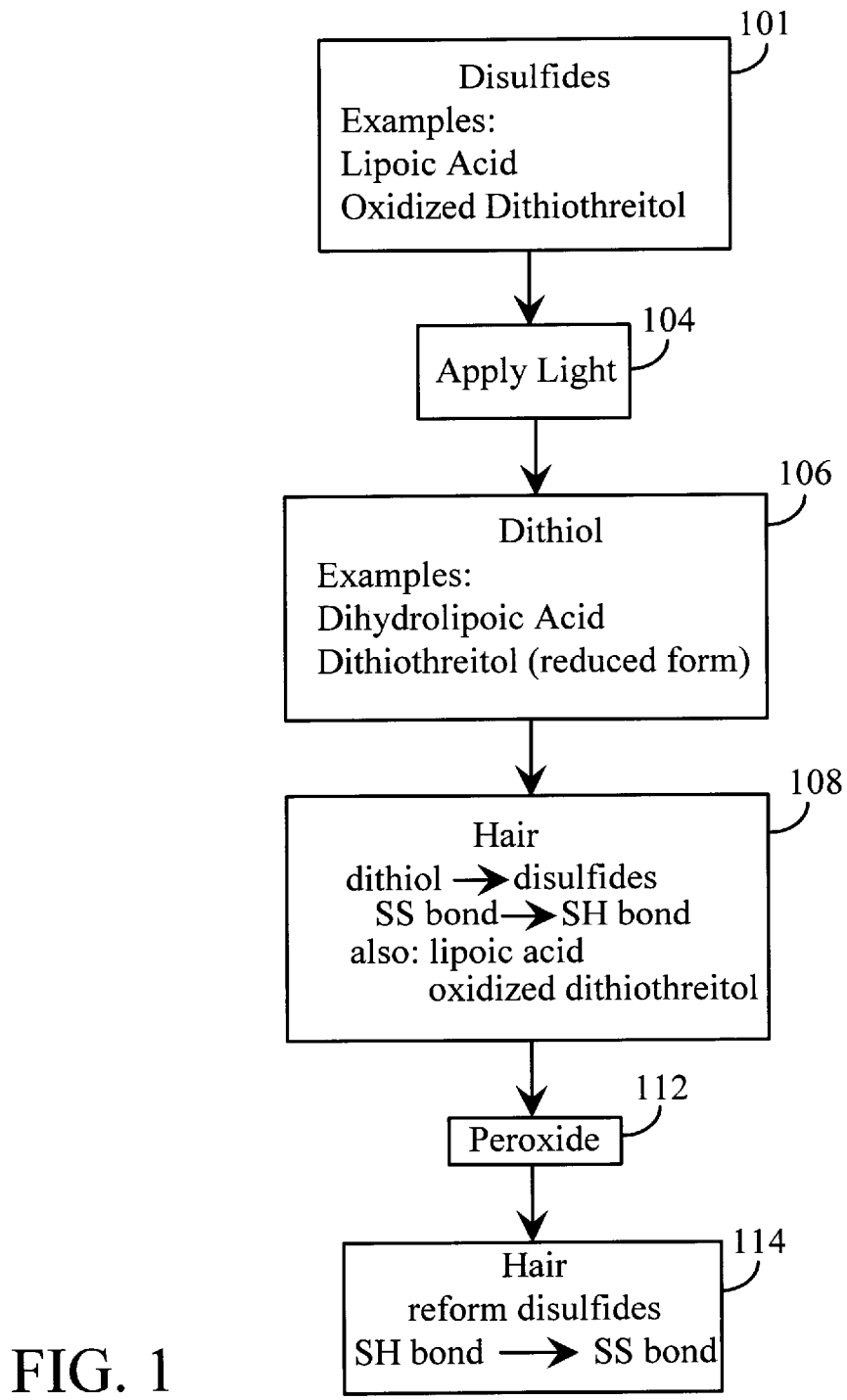
FIG. 1 is a flow diagram showing the steps in the preferred embodiment of the invention.

Hair (and other keratinic fibers) have a structure which can be described by the formula K—S—S—K, where K denotes keratin protein and S is a sulfur atom. In order to permanently alter the shape of hair, the S—S bonds in the hair must be broken and formed into sulfur hydrogen (SH) groupings. That is, the hair must be reduced to a structure K—SH where H is a hydrogen atom. When the hair is positioned in the desired shape with a curler or straightener, the S—S bonds need to be reformed so that the hair will retain its new shape.

It is known that dithiols can break the S—S bonds in hair. However, there is a problem in applying dithiols to hair in that such chemicals can irritate the skin and can cause hair cuticle damage. With the present invention, as shown in block 101, a non-irritating, non-reactive optically sensitive precursor chemical is applied to the hair. In the preferred embodiment, the optically sensitive precursor is either lipoic acid or oxidized dithiothreitol. The precursor is applied in a chemically non-reactive solution or gel formulation, and can be applied to the hair before or after wrapping the hair on a curler of the required shape.

As shown by block 104, light is then applied to the hair. The light changes the disulfide precursor chemical into a dithiol as indicated by block 106. As indicated by block 108, the dithiol reacts with the hair to break the S—S bonds and form disulfides. Some of the original precursor chemical is also reformed in the process allowing a lower initial concentration of the disulfide to be used. The hair is then styled to the desired shape. The length of time that the precursor chemical is exposed to light can be adjusted to achieve the desired amount of permanent shaping desired.

Next, as indicated by block 112, hydrogen peroxide is applied to the hair to reform the S—S bonds. This sets the hair and makes the shape applied in step 108 remain permanently. Note that this step is not required for the cyclic disulfide photosensitizers which have been found to be self-neutralizing (see discussion of FIG. 2 below).

A specific example of a self-neutralizing solution applied in step 101 is:

0.012 molar concentration of oxidized dithiothreitol (or lipoic acid) in 5 molar aqueous 2-propanol, buffered to pH 9.3 with an ammonium hydroxide/ammonium chloride buffer Solutions of 0.1–.01 molar concentration of lipoic acid or oxidized dithiothreitol are acceptable. The pH range of 7–10 is acceptable, depending on the specific photosensitizer used.

The exposure to ultraviolet (UV) light in step 104 can continue for an amount of time dependent on the effect desired. Times can range from 5 minutes to 2 hours, depending on the hair type, photosensitizer, wavelength and intensity of the light source. The photoreaction can be halted immediately when desired by simply turning off the light source.

The applied light should have a wavelength in the range of 200 to 530 nanometers ($10^{-9}$ meters). It has been found that oxidized dithiothreitol reacts best to light of about 284 nanometers and lipoic acid reacts best to light of about 330 nanometers. As explained later, other chemicals each have a preferred wavelength.

Figure 2:
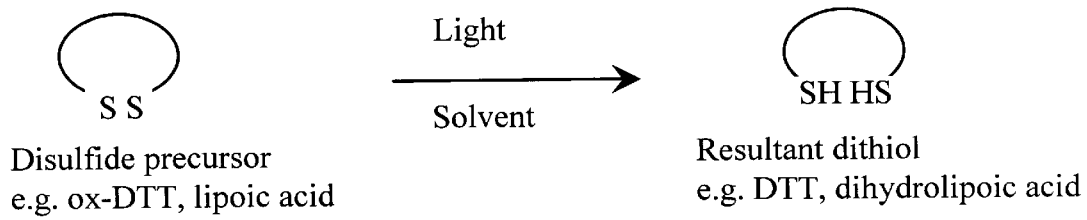
FIG. 2 is a diagram which shows the steps which constitute the present invention in a generalized form.
Figure 2:
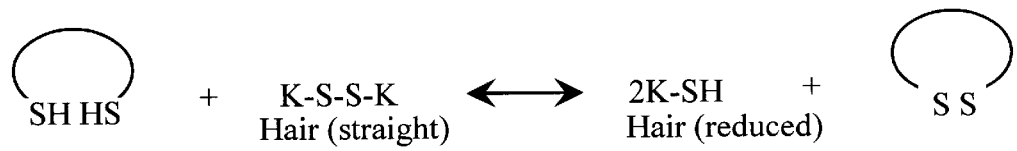
Figure 2:
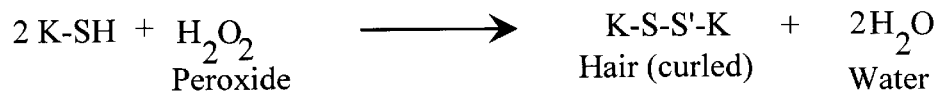

FIG. 2 shows another generalized explanation of the present invention. As shown in Step 1 of FIG. 2, light changes lipoic acid into dihydrolipoic acid. Light changes oxidized dithiothreitol (ox-DTT) into dithiothreitol (DTT). The dithiols reduce the hair disulfides, thereby breaking the S—S bonds and replacing them with SH groups. In step 2 of FIG. 2, the reaction of the dithiols with the S—S bonds in the hair also produces lipoic acid or oxidized dithiothreitol which are the precursor chemicals that started the process. It is noted that the reformation of these chemicals when the dithiols react with the hair allows the use of relatively small amounts of these chemicals initially. In addition, when these self-neutralizing disulfide photosensitizers are used, the neutralization step (Step 3 in FIG. 2) is not needed. This is because of the equilibrium (forward/reverse) nature of the reaction shown in Step 2 of FIG. 2. The principle is as follows: the dithiol reduces the S—S linkages of the hair keratin (forward reaction). This frees hair —SH residues, which can then be oxidized by the reformed disulfide, thus instantly reforming the hair S—S links (reverse reaction). The process is carried out with the hair wrapped around a curler, and the new S—S configuration is generated without the need for Step 3 in FIG. 2. The disulfide is essentially acting as a self-neutralizing photocatalyst.

It is noted that the disulfide photosensitizer essentially acts as a proton transfer agent for the hair reduction process, with the proton being provided by water and/or solvent molecules. The disulfide produced in the process is in effect recycled. It is for this reason that only a low concentration of the original disulfide photosensitizer need be used. Since the amount of photosensitizer is used here is well below the amount generally needed for a conventional chemical waving process, there is less skin irritation, less odor, and very little damage to the hair with the process described in this invention.

When the S—S bonds in the hair have been broken by photosensitizers where the self neutralization process is inefficient, as a final step, hydrogen peroxide can be applied as a neutralizer to reform the S—S bonds in the hair. Once the S—S bonds are reformed the hair will retain its new shape.

Figure 3:
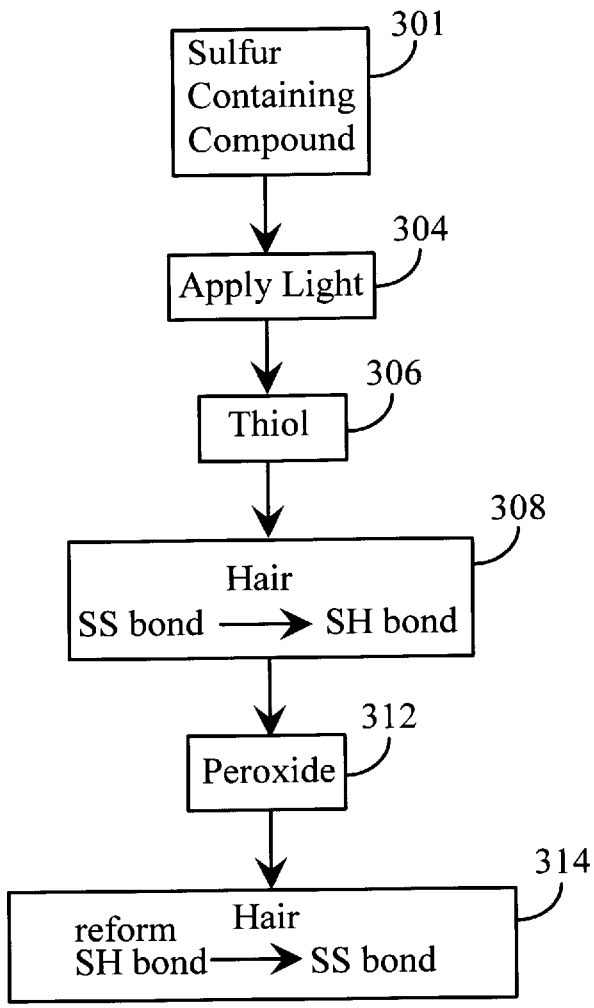
FIG. 3 is a more generalized diagram of the steps in the invention.

A more generalized presentation of the invention is shown in FIG. 3. The process begins with a photosensitive sulfur containing compound (block 301). The photosensitive sulfur containing compound is exposed to light (block 304) to form a thiol (block 306). The thiol can then react with hair (block 308) to break the S—S bonds in the hair. The hair is then shaped and a neutralizer (block 312) is applied to reform the S—S bonds (block 314). Again, this last step is not required for the self-neutralizing disulfide photosensitizers.

The wavelength of light which causes the maximum reaction of the precursor chemical depends upon the specific photosensitizer used. For example with lipoic acid the light at 330 nanometers causes the maximum reaction. With oxidized dithiothreitol, light at 284 nanometers causes the maximum reaction. A specific chemical which reacts at a desired frequency of light can be chosen.

In summary, the present invention provides a process for permanent deformation (e.g. perming) of keratinic fibers which comprises contacting the hair with a composition which contains as the active ingredient a symmetrically or unsymmetrically substituted disulfide photosensitizer of the general formula: R—S—S—R Compounds having the formula R—S—S—R are particularly valuable because when contacted with keratinic fibers such as hair and exposed to ultraviolet or visible radiation, they produce in conjunction with a solvent, reactive dithiols which very efficiently reduce the disulfide links in the keratin fiber. The keratin fiber reaction subsequently reforms the original disulfide photosensitizer for recycle. Thus a much lower concentration may be used to reduce the keratinic fiber than what is used in the conventional, purely chemical process. This is particularly true for the cyclic disulfide photosensitizers such as lipoic acid and oxidized dithiothreitol. These cyclic disulfides are also preferred because they can be formulated to make the process self-neutralizing such that Step 3 in FIG. 2 is not needed. This is because of the equilibrium nature of the reaction shown in Step 2 of FIG. 2.

The following are examples of compounds which have been found to be effective within the scope of the foregoing generic structure. The reddest absorption wavelength (range or maximum, in nanometers) of the individual example compounds is given in parentheses.

(1) Alkyl disulfides and their simple derivatives, such as R=H, $CH_3$—$(CH_2)_x$—, where x=0–7 (250 nm). Also, derivatives where the some or all of the hydrogens on the $CH_2$ groups depicted above are replaced with OH, $NH_2$, COOH, or COOX, where X is a hydrocarbon chain of 1–5 carbons in length (250 nm). Isobutyl, and tertiary butyl derivatives are also included (250 nm), along with the amino acid disulfide cystine (248 nm).

(2) Cyclic disulfides and their simple derivatives such as 1,2-dithiolane (330 nm), oxidized 1,4-dithiothreitol (284 nm), oxidized 1,4-dithioerythritol (284 nm), 1,2-dithiepane (259 nm), lipoic acid and its OH, $NH_2$, alkyl and alkali metal derivatives (330 nm), 1,4,5-oxadithiacycloheptane (300–370 nm), 3,3,5,5-tetramethyl-1,2-dithiolane (360 nm), bis-hydroxymethyl-1,2-dithiolane (330 nm), 1,2-dithiolane-4-carboxylic acid (330 nm), and $1\alpha,5\alpha$-epidithioadrostane-$3\alpha,17\beta$-diol (370 nm).

(3) Aryl disulfides and their simple derivatives such as diphenyl disulfide (260 nm), di-2-naphthyl disulfide (>320 nm), 9,9'-dianthryl disulfide (425 nm), bis-4-nitrophenyl disulfide (320 nm), bis-4-nitrophenyl phenyl disulfide (320 nm), bis-4-tolyl disulfide (320 nm), bis-4-methoxyphenyl disulfide (280 nm), 4-nitrophenyl-4'-tolyl disulfide (325 nm), 4-nitrophenyl methyl disulfide (338 nm), 2,4-dinitrophenyl methyl disulfide (331 nm), dibenzyl disulfide, and bis-2,4-dinitrophenyl disulfide (332 nm).

(4) Miscellaneous disulfides such as diacetyl disulfide, dibenzoyl disulfide, dibenzothiazoyl disulfide, and thiuram derivatives of the formula $R_2NCS-S_2-CS-NR_2$ where here R represents alkyl or alkoxy groups of 1–5 carbons in length.

As previously explained the disulfide photosensitizers in the preferred embodiment of this invention are the cyclic disulfides lipoic acid and oxidized dithiothreitol and their simple derivatives. This is because these cyclic materials are known to displace the keratin reduction reaction equilibrium towards the formation of the thiol derivative of keratin. Functional groups, which when attached to the disulfide linkage, red-shift the molecular absorption bands to wavelengths longer than 250 nm are also particularly preferred since these disulfide derivatives allow less damaging radiation to be used for the photochemical step.

Any convenient source of actinic radiation providing wavelengths in the region of the spectrum that overlaps with the absorption bands of the disulfide photosensitizers can be used to initiate the photo-production of the chemically reactive dithiol species. The light can be natural or artificial, monochromatic or polychromatic, incoherent or coherent. For high efficiency the light source should correspond closely in wavelength to the photosensitizers principle absorption bands and should be sufficiently intense to activate a substantial portion of the photosensitizer compound. The disulfide bond strength is known to be of order 54 kcal/mole. This energy corresponds to green light at 530 nm, and is the minimum energy needed to dissociate the disulfide bond. For this invention, the wavelength range from 200–530 nm (UV/Visible) may be used, depending on the absorption profile of the specific photosensitizer compound used.

Examples of conventional light sources include sunlight, fluorescent lamps, mercury, metal additive, xenon, and arc lamps, pulsed or continuous wave, providing narrow or broad spectral bands. Coherent light sources include excimer, gas, diode, and dye lasers, and the third harmonic of the neodymium YAG or glass laser (355 nm).

Solvents may include water, and a variety of straight chained and branched alcohols, glycols, and glycol ethers. Examples include, methanol, ethanol, propanol, 2-propanol, ethylene and propylene glycol, ethylene glycol monomethyl or monobutyl ether, ethylene glycol monoethyl ether acetate and the like.

It is noted that the solvent and buffer system used in the composition be reasonably transparent to the radiation used to produce the photoreaction and that it can solubilize the photosensitizer. While many known buffers solutions are employable to maintain the desired pH, one particularly preferred buffer is the ammonium chloride-aqueous ammonia system. Known thickening agents may also be used to provide the composition with the desired viscosity.

If it is desired to only shape selected portions of a person's hair the present invention can be used with the normal type of hood used by hairdressers for this type of operation. In such a case the chemicals and light are only applied to the portion of the hair one desires to shape.

While the preferred embodiments of the invention described herein show the invention applied to human hair, it should be understood that the invention can apply equally and in the same manner to reshaping other keratinic fibers which have S—S bonds.

While the invention has been described with respect to preferred embodiments thereof, it should be understood that various changes in form and detail can be made without departing from the spirit and scope of the invention. The invention is limited only by the scope of the appended claims.

I claim:

1. A method of reshaping keratinic fibers comprising the steps of:
    applying a photosensitive disulfide compound to the fibers,
    applying light to the fibers and the applied photosensitive compound,
    where the disulfide is changed into a dithiol which reacts with the keratinic fibers to break the S—S bonds in the fibers,
    shaping the fibers to the desired shape, and
    applying a neutralizer to reform the S—S bonds in the keratinic fibers.

2. The method in claim 1 wherein said photosensitive disulfide is lipoic acid.

3. The method in claim 1 wherein said photosensitive disulfide is oxidized dithiothreitol.

4. The method of claim 1 wherein said neutralizer is peroxide.

5. The method in claim 1 wherein said photosensitive disulfide is an alkyl disulfide.

6. The method in claim 1 wherein said photosensitive disulfide is a cyclic disulfide.

7. The method in claim 1 wherein said photosensitive disulfide is an aryl disulfide.

8. The method in claim 1 wherein said photosensitive disulfide is a derivative of an alkyl disulfide.

9. The method in claim 1 wherein said photosensitive disulfide is a derivative of a cyclic disulfide.

10. The method in claim 1 wherein said photosensitive disulfide is a derivative of an aryl disulfide.

11. The method recited in claim 1 wherein the light has a wavelength in the range of 200 to 530 nanometers.

12. A method of permanently waving hair which includes S—S bonds, comprising the steps of:
    applying a photosensitive disulfide compound selected from the group consisting of lipoic acid and oxidized dithiothreitol,
    applying light to photolyze the photosensitive compound into a dithiol, where the dithiol reacts with the hair to break the S—S bonds in the hair,
    shaping the hair to the desired shape, and
    applying a neutralizer to reform the S—S bonds in the hair.

13. A self neutralizing method of reshaping keratinic fibers comprising the steps of:

applying a photosensitive disulfide compound to the fibers, applying light to the fibers and the applied photosensitive compound, where the disulfide is changed into a dithiol which reacts with the keratinic fibers to break the S—S bonds in the fibers, and shaping the fibers to the desired shape.

14. A method of reshaping keratinic fibers comprising the steps of:

applying to the fibers a photosensitive disulfide compound which has the formula R—S—S—R, where R represents alkyl or alkoxy groups of 1–5 carbon atoms in length and S represents a sulfur atom, applying light to the fibers and the applied photosensitive compound, where the disulfide is changed into a dithiol which reacts with the keratinic fibers to break the S—S bonds in the fibers, shaping the fibers to the desired shape, and applying a neutralizer to reform the S—S bonds in the keratinic fibers.

15. A method of waving hair comprising the steps of:

applying an disulfide optical photosensitizer to the hair, exposing said hair to natural or artificial light of sufficient intensity to produce a thiol or dithiol from said disulfide, forming said hair to a desired shape, and applying a neutralizing agent to said hair.

16. A method of reshaping keratinic fibers which contain S—S bonds comprising the steps of:

applying a photosensitive sulfide containing compound to the fibers, apply light to the fibers and the applied photosensitive compound, where a thiol is formed which reacts with the keratinic fibers to break the S—S bonds in the fibers, and shaping the fibers to the desired shape.

\* \* \* \* \*